(12) United States Patent
Murakami et al.

(10) Patent No.: US 9,114,213 B2
(45) Date of Patent: Aug. 25, 2015

(54) PHARMACEUTICAL INJECTION DEVICE

(71) Applicant: PANASONIC HEALTHCARE HOLDINGS CO., LTD., Minato-Ku, Tokyo (JP)

(72) Inventors: Kenji Murakami, Ehime (JP); Mitsuteru Fujimoto, Ehime (JP); Toshiaki Iio, Ehime (JP)

(73) Assignee: Panasonic Healthcare Holdings Co., Ltd., Minato-Ku, Tokyo ( * ) Notice: Subject to any disclaimer, the term of this patent is extended or adjusted under 35 U.S.C. 154(b) by 0 days.

(21) Appl. No.: 14/366,262

(22) PCT Filed: Dec. 11, 2012

(86) PCT No.: PCT/JP2012/007906
§ 371 (c)(1),
(2) Date: Jun. 17, 2014

(87) PCT Pub. No.: WO2013/099123
PCT Pub. Date: Jul. 4, 2013

(65) Prior Publication Data
US 2014/0330199 A1 Nov. 6, 2014

(30) Foreign Application Priority Data

Dec. 26, 2011 (JP) .................................. 2011-283215

(51) Int. Cl.
*A61M 31/00* (2006.01)
*A61M 5/20* (2006.01)
(Continued)

(52) U.S. Cl.
CPC . *A61M 5/20* (2013.01); *A61M 5/24* (2013.01); *A61M 5/315* (2013.01);
(Continued)

(58) Field of Classification Search
CPC ................... A61M 2205/103; A61M 2205/50; A61M 5/20; A61M 5/24; A61M 2005/31588; A61M 2205/14; A61M 2205/3317; A61M 2205/3368; A61M 2205/3372; A61M 5/31568; G06F 19/3468
USPC ........................................................... 604/67
See application file for complete search history.

(56) References Cited

U.S. PATENT DOCUMENTS 4,850,805 A 7/1989 Madsen et al.
(Continued)

FOREIGN PATENT DOCUMENTS

| CN | 101432601 A | 5/2009 |
| CN | 102233148 A | 11/2011 |

(Continued)

OTHER PUBLICATIONS

The International Search Report from No. PCT/JP2012/007906 Issued on Mar. 12, 2013.
(Continued)

*Primary Examiner* — Jason Flick
(74) *Attorney, Agent, or Firm* — Shinjyu Global IP

(57) ABSTRACT

The pharmaceutical injection device comprises a syringe mounting portion configured to mount thereon a syringe containing a drug, the syringe including at a front end side thereof an injection needle mounting portion on which an injection needle is mounted and a gasket at a rear end side thereof, a plunger operable to press the gasket in the syringe mounted on the syringe mounting portion toward the injection needle mounting portion, a motor operable to drive the plunger, an encoder operable to detect a rotation amount of the motor, and a controller connected to the encoder and operable to control a driving of the motor. The controller is operable to obtain a motor rotation amount that corresponds to a deformation amount of the gasket deformed by the plunger, and control a rotation of the motor at a time of injection of the drug in accordance with the motor rotation amount.

15 Claims, 18 Drawing Sheets

(51) Int. Cl.
*A61M 5/24* (2006.01)
*G06F 19/00* (2011.01)
*A61M 5/315* (2006.01)

(52) U.S. Cl.
CPC ....... *G06F 19/3468* (2013.01); *A61M 5/31568* (2013.01); *A61M 2005/31588* (2013.01); *A61M 2205/103* (2013.01); *A61M 2205/14* (2013.01); *A61M 2205/3317* (2013.01); *A61M 2205/3368* (2013.01); *A61M 2205/3372* (2013.01); *A61M 2205/50* (2013.01)

(56) References Cited

U.S. PATENT DOCUMENTS

| | | |
|---|---|---|
| 7,500,959 B2 | 3/2009 | Munk |
| 7,959,609 B2 | 6/2011 | Gaydos et al. |
| 8,147,447 B2 | 4/2012 | Sundar et al. |
| 8,147,448 B2 | 4/2012 | Sundar et al. |
| 2002/0107486 A1* | 8/2002 | Munk .......................... 604/209 |
| 2007/0066938 A1* | 3/2007 | Iio et al. ........................ 604/152 |
| 2007/0073228 A1 | 3/2007 | Mernoe et al. |
| 2008/0308580 A1 | 12/2008 | Gaydos et al. |
| 2010/0211003 A1* | 8/2010 | Sundar et al. ................... 604/67 |
| 2010/0292635 A1* | 11/2010 | Sundar .......................... 604/67 |
| 2011/0097229 A1* | 4/2011 | Cauley, III et al. ........... 417/518 |

FOREIGN PATENT DOCUMENTS

| | | |
|---|---|---|
| EP | 0282323 B1 | 5/1994 |
| EP | 2384778 A1 | 11/2011 |
| JP | S63-248988 A | 10/1988 |
| JP | 2004-510505 A | 4/2004 |
| JP | 2007-111518 A | 5/2007 |
| JP | 2009-526565 A | 7/2009 |
| JP | 2010-538799 A | 12/2010 |
| WO | 2007/094833 A1 | 8/2007 |
| WO | 2011/113806 A1 | 9/2011 |
| WO | 2011/141907 A1 | 11/2011 |

OTHER PUBLICATIONS

Supplementary European Search Report from the corresponding European Patent Application No. 12861993.9 issued on May 4, 2015.
Office Action from the corresponding Chinese Patent Application No. 201280063661.8 issued on Jun. 3, 2015.

* cited by examiner

PHARMACEUTICAL INJECTION DEVICE

PRIORITY

This application claims priority to International Application No. PCT/JP2012/007906, with an international filing date of Dec. 11, 2012 which claims priority to Japanese Patent Application No. 2011-283215 filed on Dec. 26, 2011. The entire disclosures of International Application No. PCT/JP2012/007906 and Japanese Patent Application No. 2011-283215 are hereby incorporated herein by reference.

TECHNICAL FIELD

The present disclosure relates to a pharmaceutical injection device using a pharmaceutical syringe containing a drug. Particularly, it relates to a pharmaceutical injection device for injecting a body with a drug with high pressure.

BACKGROUND

A pharmaceutical injection device includes an injection needle mounting portion at its front end, a syringe mounting portion at its rear end for mounting thereon a syringe having a gasket, a plunger for pressing the gasket of the syringe mounted on the syringe mounting portion toward the injection needle mounting portion, a motor for driving the plunger, an encoder for detecting a rotation frequency of the motor, a controller connected to the encoder, and a memory connected to the controller.

Particularly, the plunger is driven by the motor to press the gasket toward the injection needle mounting portion, and then, the drug is injected through the injection needle into a human body, for example.

Meanwhile, the rotation frequency of the motor is detected by the encoder, and the injection amount of a drug is controlled so as to be a set amount. However, because of a considerable variation in part accuracy, it was difficult to perform a drug injection in a set injection amount.

In order to prevent this, one method has been proposed in which a relation between the rotation frequency detected by the encoder and the drug injection amount is stored in a memory, and the rotation frequency of the motor is controlled based on the data stored in the memory (See, patent Literature 1: Japanese Patent Publication JP2004-510505).

SUMMARY

In the above known method, the rotation frequency of a motor is controlled based on the data stored in a memory, which could suppress a variance in the injection amount of a drug caused by a variance in part accuracy. With the above known method, however, the following issues would arise.

Conventionally, a needle with a size of 24 G, which is 0.57 mm in outer diameter and 0.31 mm in inner diameter, was used for subcutaneous injections. In recent years, however, a thinner injection needle has been demanded to ease pain at the time of needling. Owing to an improvement in processing technology, a thin injection needle with a size of 30 G, which is 0.31 mm in outer diameter and 0.16 mm in inner diameter, has come into general use. Moreover, thinner needles with a size of 31 to 33 G have been mass-produced. Therefore, even when a pharmaceutical injection device having the configuration according to the above known example is used, if a thin needle injection is used for injections, the injection amount of drug could vary widely.

Specifically, when a known thick injection needle is used, the injection needle has a flow path with less resistance. Therefore, if the gasket is pressed by the plunger, a certain amount of drug that is equal to a pressing amount of the plunger can be injected into a body. However, when a thinner injection needle is used, the flow path has an increased resistance. In this case, if the gasket is pressed by the plunger, the gasket is compressed and therefore, a proper amount of drug can not be injected into a body.

In particular, in a case where a thin injection needle is used for drug injections or in such other cases, a large force is needed to push a drug out of the injection needle. In such a situation that the drug does not flow out of the injection needle smoothly, the gasket is compressed between the plunger and the drug. This compression of the gasket prevent the drug from being injected into a body properly.

Accordingly, the present invention aims to perform a drug injection properly.

The pharmaceutical injection device of the present disclosure is a pharmaceutical injection device for injecting a set injection amount of a drug and comprises a syringe mounting portion, a plunger, a motor, an encoder, and a controller. The syringe mounting portion is configured to mount thereon a syringe containing the drug. The syringe includes at a first end side thereof an injection needle mounting portion on which an injection needle is mounted and an elastic member at a second end side thereof. The plunger is operable to press the elastic member in the syringe mounted on the syringe mounting portion toward the injection needle mounting portion. The motor is operable to drive the plunger. The encoder is operable to detect a rotation amount of the motor. The controller is connected to the encoder and operable to control a driving of the motor. The controller is further operable to obtain a first motor rotation amount that corresponds to a deformation amount of the elastic member deformed by the plunger, and control a rotation of the motor at a time of drug injection in accordance with the first motor rotation amount.

The pharmaceutical injection device of the present disclosure performs a drug injection properly.

DETAILED DESCRIPTION

Embodiments of the present invention will be discussed in detail with reference to the accompanying drawings. It will be apparent to those skilled in the art from this disclosure that the following descriptions of the embodiments are provided for illustration only and not for the purpose of limiting the invention as defined by the appended claims and their equivalents.

1. First Embodiment 1-1 Configuration

FIG. 1 to FIG. 4 show an example of a pharmaceutical injection device 100 according to this embodiment.

Figure 1:
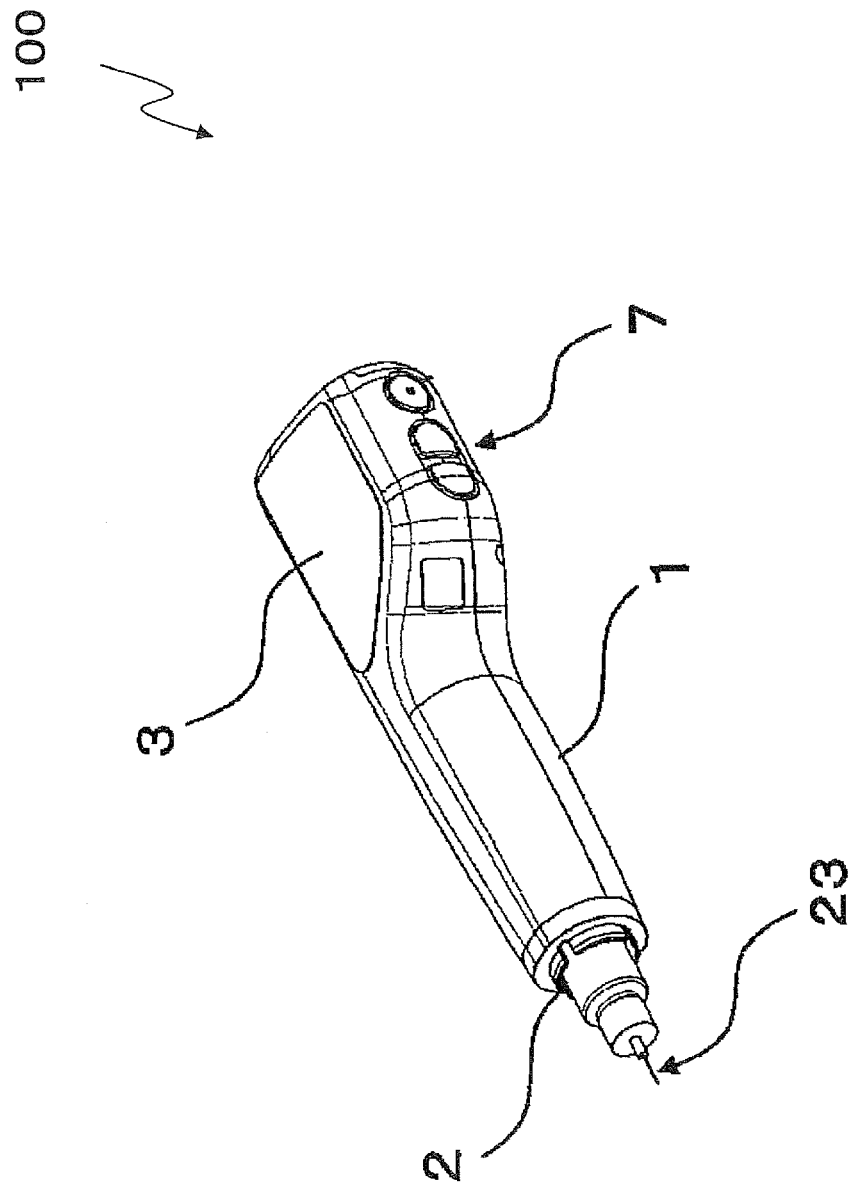
FIG. 1 is a schematic perspective view of a pharmaceutical injection device according to the first embodiment.
Figure 2:
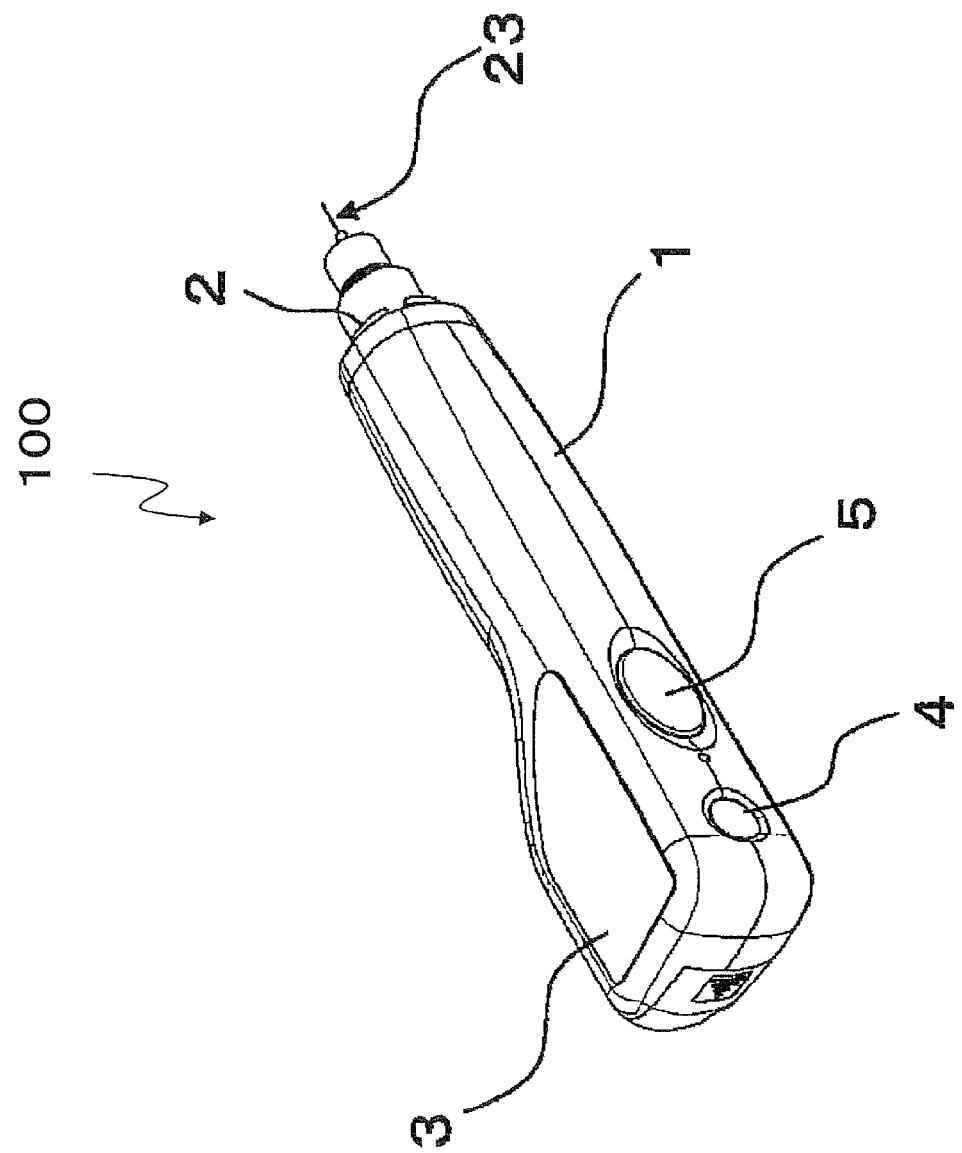
FIG. 2 is a schematic perspective view of the pharmaceutical injection device when viewed from another angle.

As shown in FIG. 1 and FIG. 2, the pharmaceutical injection device 100 comprises a body case 1, a syringe mounting portion 2 (an example of a syringe mounting portion) provided at one end side of the body case 1, and a display portion 3 provided at the other end side of the body case 1. The pharmaceutical injection device 100 further comprises, at the other end side, a power button 4, a drug injection button 5 (an example of a second mode start switch), and a preset button 7. Note that the number, the position, the shape, the size, etc. of these buttons shown in the drawings are just an example and should not be considered as the only option.

Figure 3:
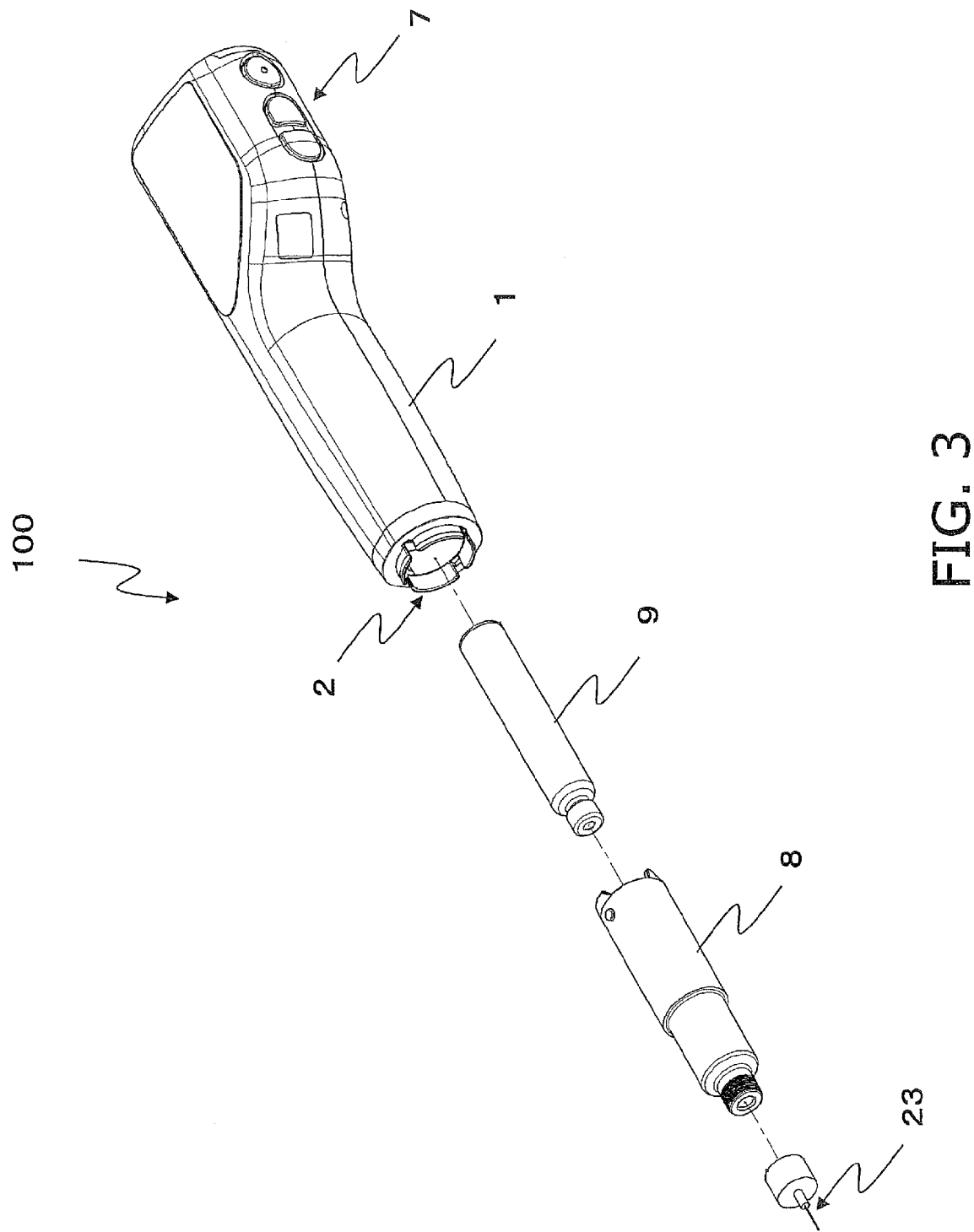
FIG. 3 is a schematic exploded perspective view of the pharmaceutical injection device.
Figure 4:
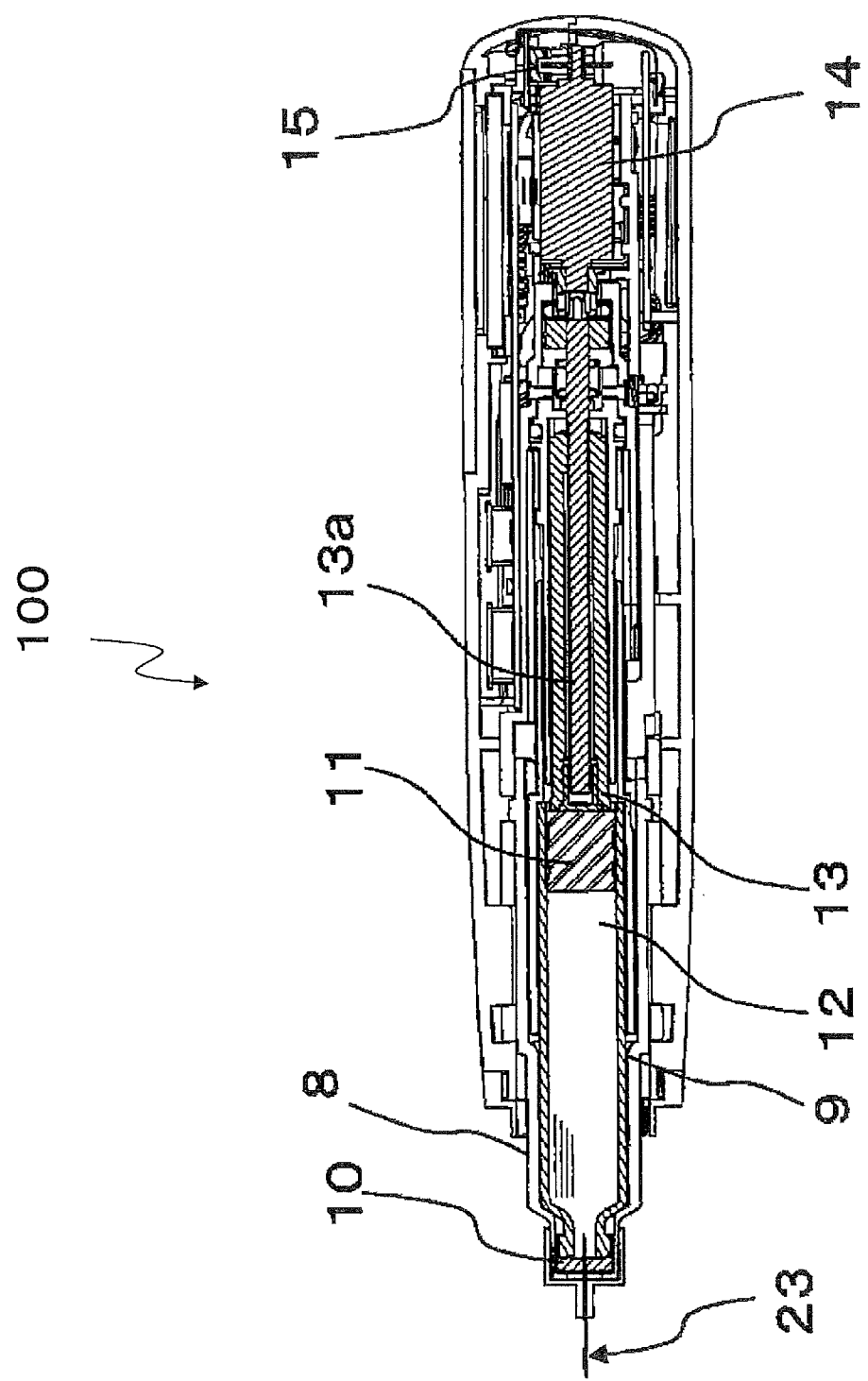
FIG. 4 is a schematic section view of the pharmaceutical injection device.

The syringe mounting portion 2 of the case body 1 is configured to be covered by a syringe cover 8, as shown in FIG. 3 and FIG. 4. More specifically, the syringe mounting portion 2 has such a configuration that a syringe 9 housed in the syringe cover 8 can be mounted on the syringe mounting portion 2. The syringe 9 has at its front end side an injection needle mounting portion 10 (an example of an injection needle mounting portion). The rear end side of the syringe 9 has a cylinder shape having a gasket 11 (an example of an elastic member). The inside of the syringe 9 is filled with a drug 12 that is effective against various kinds of diseases.

Inside of the body case 1, as shown in FIG. 4, there are a plunger 13 (an example of a plunger) for pressing the gasket 11 of the syringe 9 mounted on the syringe mounting portion 2 toward the injection needle mounting portion 10, a motor 14 (an example of a motor) for driving the plunger 13 with a feed screw 13a, an encoder 15 (an example of an encoder) for detecting a rotation frequency of the motor 14 (an example of a motor rotation amount), a current detection sensor 16 (FIG. 5; an example of a current detection sensor) for detecting a current flowing in the motor 14, a controller 17 (FIG. 5; an example of a controller) connected to the current detection sensor 16, the encoder 15, etc., and a memory 18 (FIG. 5) connected to the controller 17.

Figure 5:
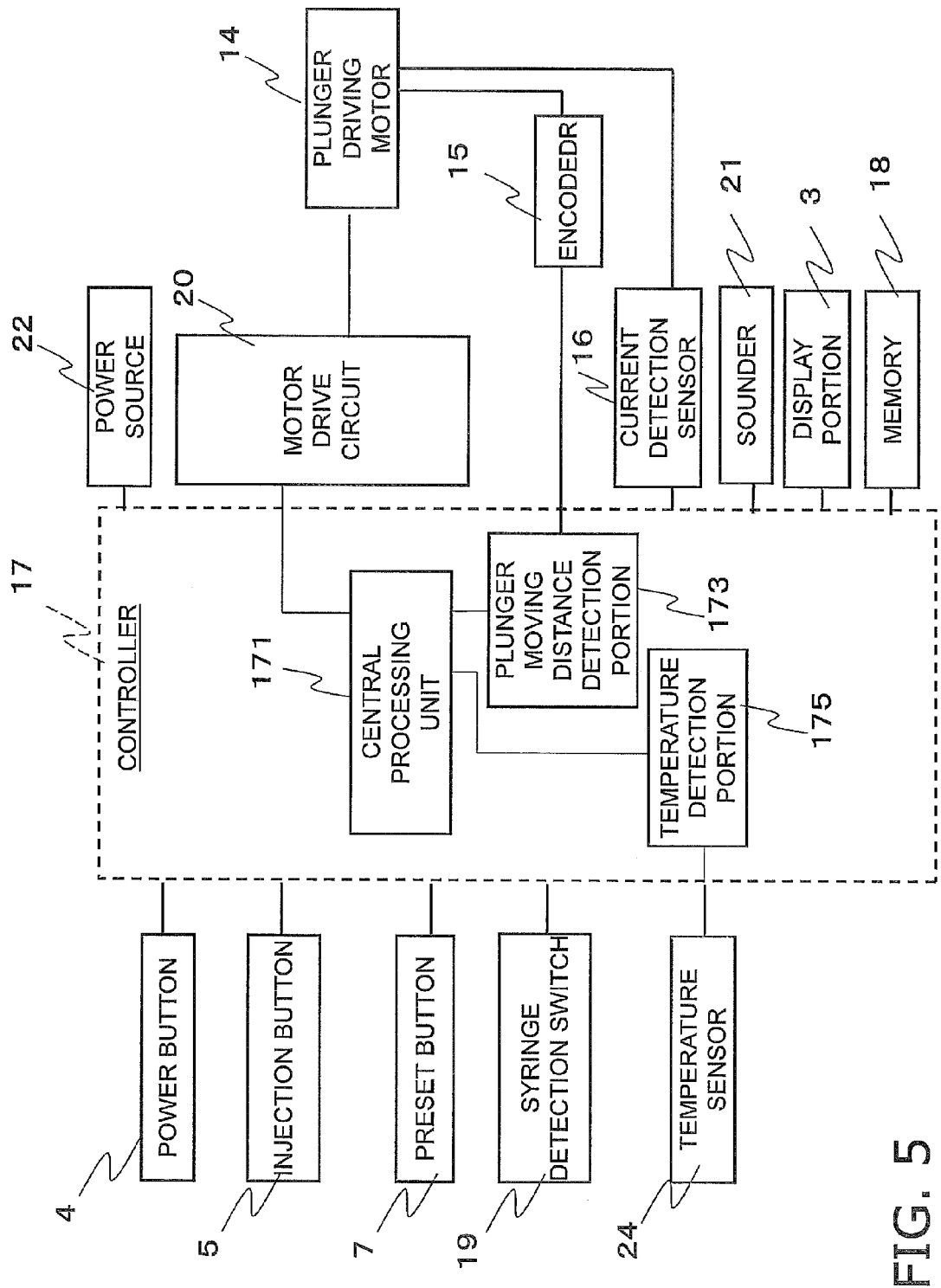
FIG. 5 is a control block diagram of the pharmaceutical injection device.

FIG. 5 is a control block diagram of the pharmaceutical injection device 100 according to this embodiment. The pharmaceutical injection device 100 includes a controller 17. The controller 17 includes a central processing unit 171 comprised of for example, a processor (CPU, for example) that executes a predetermined program for performing functions of the portions shown in FIG. 5. The controller 17 also includes functions of a plunger moving distance detection portion 173 and a temperature detection portion 175, and such other portions. The plunger moving distance detection portion 173 calculates a moving distance of the plunger based on a motor rotation frequency detected by the encoder 15, which will be described later. The temperature detection portion 175 determines an ambient temperature of the syringe 9 detected by the temperature sensor 24. The temperature sensor 24 or the temperature detection portion 175 is not necessarily required for the pharmaceutical injection device 100 according to this embodiment.

The memory 18 connected to the controller 17 stores, for example, a program to be executed by the controller 17 and data to be processed by execution of the program.

According to this embodiment, a syringe detection switch 19 (FIG. 5) is provided. The syringe detection switch 19 is connected to the controller 17 and detects whether the syringe 9 has been mounted on the syringe mounting portion 2. The motor 14 is connected to the controller 17 via a motor drive circuit 20. The controller 17 is also connected to the display portion 3, the power button 4, the injection button 5, the preset button 7, the current detection sensor 16, the syringe detection switch 19, and the sounder 21. The controller 17 is connected to the power source 22 comprised of a battery cell and a power circuit, and controls a power supply to the pharmaceutical injection device 100.

1-2 Operation

One characteristic point of the pharmaceutical injection device 100 according to this embodiment is that the controller 17 regulates an initial setting mode for an injection amount and a drug injection mode.

1-2-1 Initial Setting Mode for Injection Amount

Firstly, the initial setting mode for an injection amount will be explained mainly by reference to FIG. 6 (from S601 to S603) and FIG. 7, Before the initial setting mode for an injection amount is started, a syringe 9 that is housed in the syringe cover 8 is mounted on the syringe mounting portion 2, as shown in FIG. 4.

Although FIG. 4 shows an injection needle 23 mounted on the injection needle mounting portion 10 of the syringe 9, an injection needle 23 is not mounted on the injection needle mounting portion 10 in the initial setting mode for an injection amount.

When a syringe 9 is mounted on the syringe mounting portion 2, the syringe detection switch 19 detects that the syringe 9 is mounted and the controller 17 determines whether the syringe detection switch 19 has detected the mounting or not (S601).

Since the power button 4 has been pressed to power on the device at this time, if the controller 17 determines that no detection of the syringe mounting is made by the syringe detection switch 19, the controller 17 controls the display portion 3 so as to display a message such as "Please mount a syringe" (S602).

On the other hand, if the controller 17 determines that the syringe detection switch 19 has detected that a syringe 9 is mounted properly, the controller 17 performs an initial setting process for an injection amount (S603).

(Initial Setting Process for Injection Amount)

Figures 6, 7:
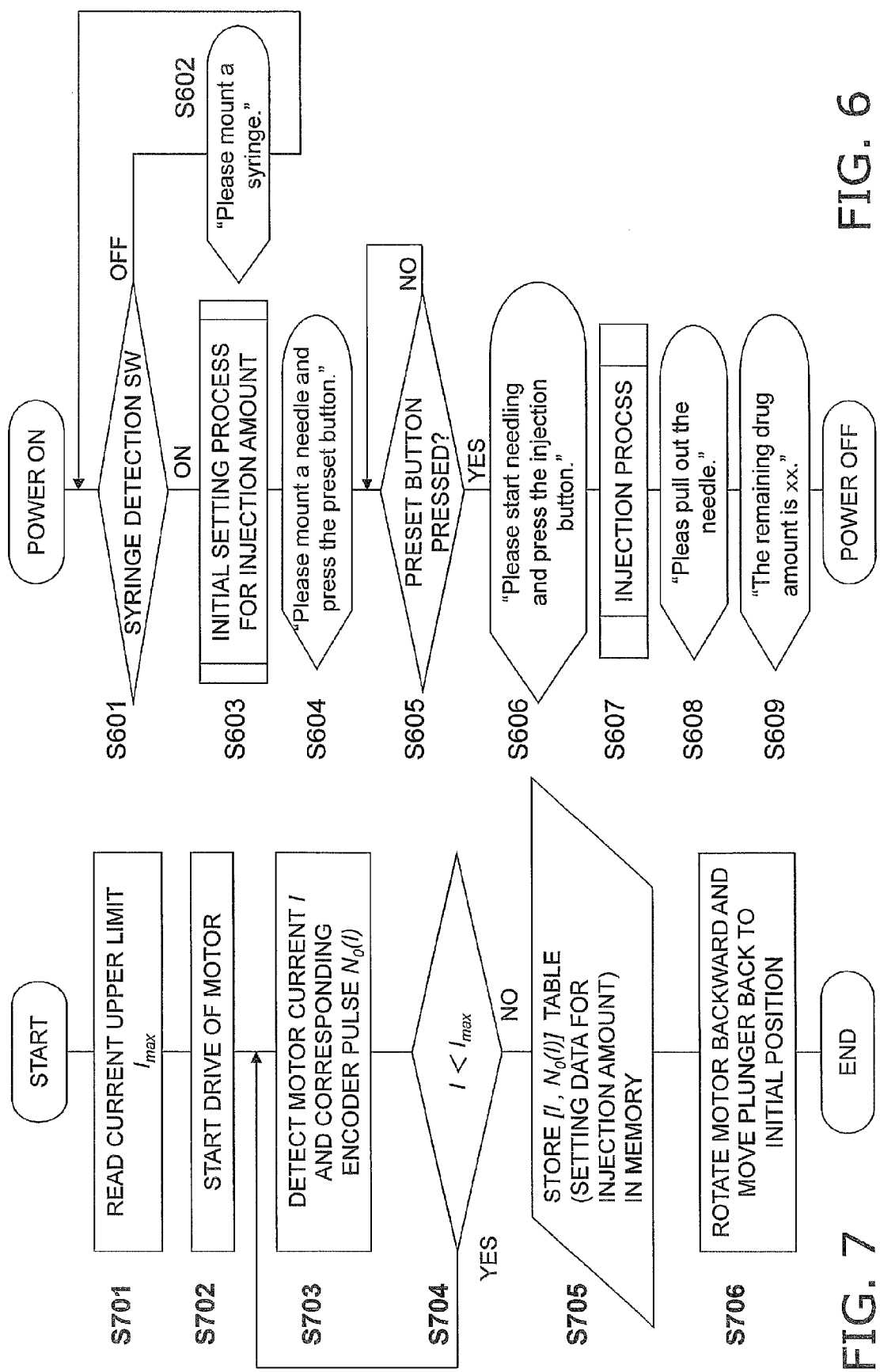
FIG. 6 is a flow chart of an operation of the pharmaceutical injection device.
FIG. 7 is a flow chart of an operation of the pharmaceutical injection device.

The initial setting process for an injection amount is performed as shown in FIG. 7.

The controller 17 reads a value of the current upper limit value $I_{max}$ in FIG. 7, which has been stored in the memory 18 (S701).

Next, the controller 17 drives the motor 14 so that the gasket 11 is pressed toward the injection needle mounting portion 10 with the feed screw 13a and the plunger 13 (S702).

At this time, the rotation frequency of the motor 14 is detected by the encoder 15, at the time of which the motor current I is detected by the current detection sensor 16 (S703).

Figure 9:
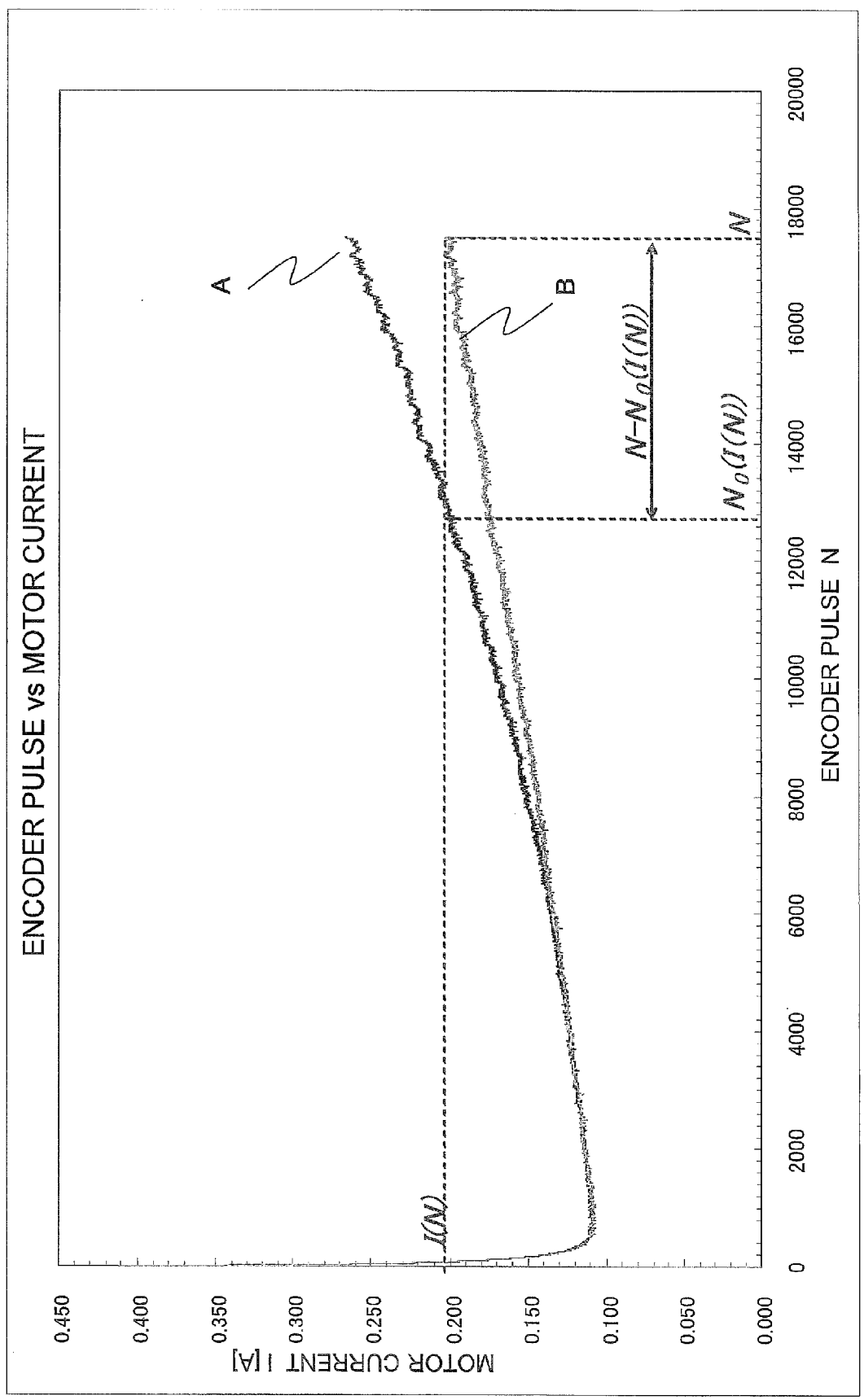
FIG. 9 shows an example of a characteristic of an operation of the pharmaceutical injection device.

When the current detection sensor 16 detects that the motor current I has reached or surpassed the value of $I_{max}$ (S704), the controller 17 stops driving the motor 14. The obtained data indicating a characteristic (such as characteristic A shown in FIG. 9) are stored in the memory 18 in the form of Table [I, $N_0(I)$] (S705). In this embodiment, "I" expresses a motor current, and $N_0(I)$ expresses the number of encoder pulses (an example of a first motor rotation amount).

After that, the controller 17 rotates the motor 14 backward to move the plunger 13 back to its initial position (S706).

At this time, an injection needle 23 is not mounted on the injection needle mounting portion 10 of the syringe 9. Therefore, as described above, even if the plunger 13 presses the gasket 11, the drug 12 contained in the syringe 9 is not compressed, but only the gasket 11 is compressed in a direction toward the injection needle mounting portion 10. Accordingly, if the plunger 13 is moved back to its initial position by a backward rotation of the motor 14, the gasket 11 which has been compressed is also restored to its original state, as shown in FIG. 4.

1-2-2 Drug Injection Mode

Next, the drug injection mode will be described mainly by reference to FIG. 6 (from S604 to S609) and FIG. 8. The drug injection mode is implemented after the initial setting mode for an injection amount is completed.

The controller 17 controls the display portion 3 so as to display information that prompts a user to mount the injection needle 23 and press the preset button 7 (S604).

When the needle 23 is mounted and the preset button 7 is pressed by the user (S605), the controller 17 controls the display portion 3 so as to display information that prompts the user to shove the injection needle 23 as shown in FIG. 1, FIG. 2 and FIG. 4 into his/her body and press the drug injection button 5 (S606).

Figure 8:
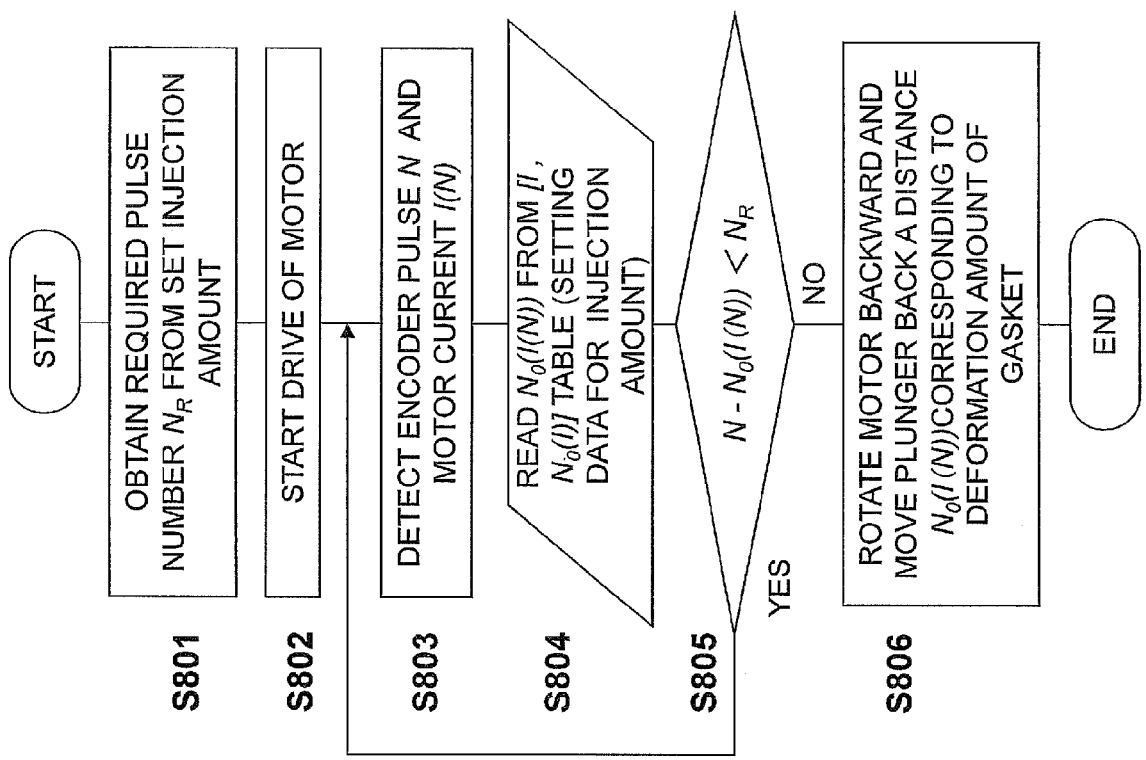
FIG. 8 is a flow chart of an operation of the pharmaceutical injection device.

When the drug injection button 5 is pressed by the user, the process goes to an injection process as shown in FIG. 8 (S607). Then, the drug injection mode as shown in FIG. 8 is started.

The memory 18 stores a value for the number of encoder pulses that has been set in advance. The number of encoder pulses corresponds to the rotation frequency of the motor 14 corresponding to a set injection amount that is a target dosage amount of the drug 12. In this embodiment, the number of encoder pulses corresponding to the set injection amount of the drug 12 is expressed by "$N_R$" (an example of a third motor rotation amount). The "$N_R$" is calculated by the following formula, for example.

$$N_R = P_0 * R * V / (L * A) \quad \text{(Formula 1)}$$

$P_0$: a number of encoder pulses per a single rotation of a motor

R: a reduction ratio of a geared motor
L: a pitch for a feed screw
A: a section area of a syringe
V: a set injection amount The controller 17 obtains, from the memory 18, the number of encoder pulses $N_R$ that corresponds to the set injection amount (S801). In step S801, the controller 17 may calculate the number of encoder pulses based on a set injection amount obtained according to a predetermined program.

Next, the controller 17 drives the motor 14 to press the gasket 11 toward the injection needle mounting portion 10 with the feed screw 13a and the plunger 13 (S802).

During this, a rotation frequency of the motor 14 is detected by the encoder 15, and the motor current is detected by the current detection sensor 16 (S803). As a result, the controller 17 obtains a certain characteristic (such as characteristic B shown in FIG. 9). While the characteristic B is being obtained, the encoder 15 and the current detection sensor 16 keep detecting the rotation frequency (N) of the motor 14 and the motor current I (N) (an example of a second motor rotation amount), respectively, in the drug injection mode.

The controller 17 reads, from the memory 18, the rotation frequency of the motor or the number of encoder pulses $N_0$ (I(N)) when the current corresponding to the motor current I(N) flows, according to the characteristic A (S804).

Then, while a difference between the number of encoder pulses (N) and the number of encoder pulses $N_0$ (I(N)) is less than the above described rotation frequency ($N_R$), the motor 14 is being driven (from S803 to S805 in FIG. 8).

When a difference between the number of encoder pulses (N) and the number of encoder pulses $N_0$ (I(N)) goes over the above described rotation frequency ($N_R$), the injection of drug is stopped, and the motor 14 is rotated backward by an amount that corresponds to $N_0$ (I(N)), or a deformation amount of the gasket 11 (S806 in FIG. 8).

According to this embodiment, attention is focused on the fact that with the same motor current, the rotation frequency of the motor 14 differs between the initial setting mode for an injection amount and the drug injection mode. In particular, in the initial setting mode for an injection amount, an injection needle 23 is not mounted on the syringe 9 as discussed above, and therefore, the detected motor current will be a current that is needed for the plunger 13 to only compress the gasket 11. In other words, the detected motor current corresponds to a deformation amount of the gasket 11. In the drug injection mode on the other hand, the injection needle 23 is mounted on the syringe 9, and therefore, the detected motor current will be a current that is needed for the plunger 13 not only to compress the gasket 11 but also to push the drug 12 out of the syringe 9 for injection. This means that the target injection amount is obtained when a difference between the number of encoder pulses $N_0$ (I(N)) in the initial setting mode for an injection amount and the number of encoder pulses N in the drug injection mode reaches the number of encoder pulses ($N_R$) that corresponds to the set injection amount of the drug 12, with the same motor current.

In this embodiment, therefore, the operation of S701 to S705 in FIG. 7 is performed, which enables the device to inject a set amount of drug into a body even when the drug 12 is pressed with high pressure.

When a proper amount of drug has been thus injected into a body, the controller 17 rotates the motor 14 backward by the amount of $N_0$ (I(N)), and moves the plunger 13 back (S806 in FIG. 8). As discussed above, the number of encoder pulses $N_0$ (I(N)) at this point corresponds to an amount of compression of the gasket 11 at the time of completion of the drug injection. Therefore, the plunger 13 is moved back through a distance corresponding to that amount, so that the compressed gasket 11 is restored to its original shape. The motor 14 may be rotated backward more than the $N_0$ ((N). In this case, however, the gasket 11 will be separated from the plunger 13, and therefore, it is necessary to move the plunger 13 forward through a distance corresponding to that excess rotation at a next operation.

After that, the controller 17 controls the display portion 3 so as to display information that prompts the user to pull the injection needle out of his/her body (S608). Finally, the display portion 3 displays the remaining amount of drug (S609), and the power is turned off.

1-3 Effects

In this embodiment, the pharmaceutical injection device 100 comprises: a syringe mounting portion 2 configured to mount thereon a syringe 9 containing a drug 12, the syringe 9 including at its front end side an injection needle mounting portion 10 on which an injection needle 23 is mounted and a gasket 11 at its rear end side; a plunger 13 operable to press the gasket 11 in the syringe 9 mounted on the syringe mounting portion 2 toward the injection needle mounting portion 10; a motor 14 operable to drive the plunger 13; an encoder 15 operable to detect a rotation frequency of the motor 14; and a controller 17 connected to the encoder 15 and operable to control a driving of the motor 14. The controller 17 is operable to obtain a rotation frequency of the motor that corresponds to a deformation amount of the gasket 11 due to the press of the plunger 13 by the plunger 13, namely the number of encoder pulses $N_0$, and control a rotation of the motor at the time of injection of the drug 12 in accordance with the obtained rotation frequency of the motor. With this configuration, it is possible to perform a drug injection taking into account a deformation amount of the gasket 11. As a result, it is possible to perform a drug injection with adequate pressure.

Particularly, since the gasket 11 is generally produced using a mold that is capable of producing multiple gaskets, such molded gaskets vary in shape and size. Furthermore, the rubber material used for producing the gasket 11 changes its hardness with temperature. Therefore, each gasket 11 is deformed by the plunger 13 according to its own deformation characteristic, which is given by an individual difference of each syringe 9. Also, the gasket 11 varies according to the ambient temperature when it is used. The pharmaceutical injection device 100 according to this embodiment obtains a deformation characteristic of the gasket 11 by measuring the actual rotation frequency of the motor 14 before a drug injection, namely the rotation amount of the motor 14 corresponding to a deformation amount of the gasket 11, and the corresponding current values. The pharmaceutical injection device 100 then determines a motor rotation amount at the time of the drug injection based on the deformation characteristic. As a result, the variance of the gasket 11 in size or the hardness change of the gasket 11 are cancelled out, which achieves a drug injection with a high degree of accuracy.

1-4 Modified Examples (1)

Figure 10:
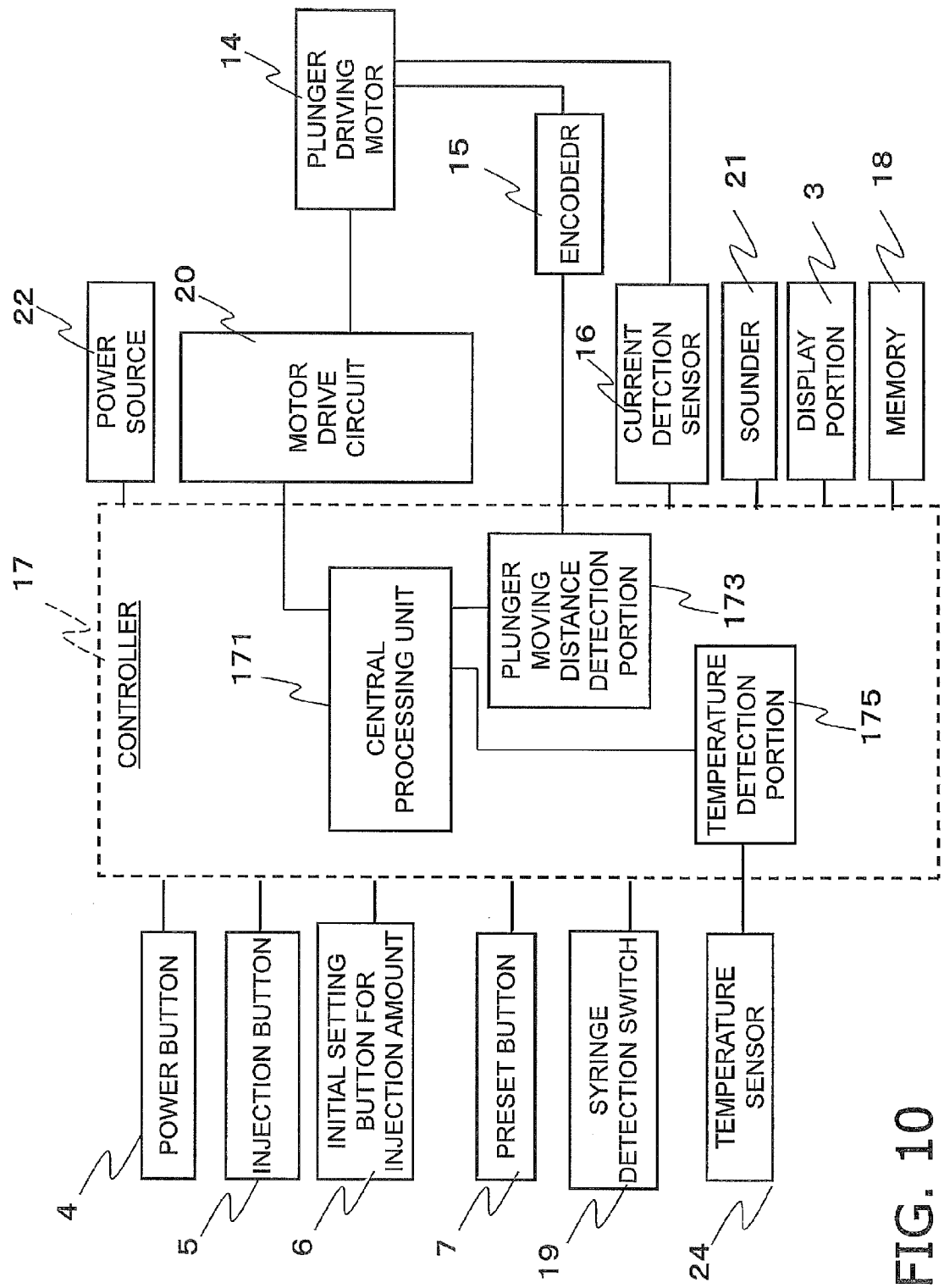
FIG. 10 is a control block diagram of the pharmaceutical injection device according to a modified example of the first embodiment.

In the above embodiment, the controller 17 automatically transfers to the initial setting mode for an injection amount after detecting the mounting of the syringe 9, but this is not the only option. As shown in FIG. 10, the device may be provided with an initial setting button 6 for an injection amount (an example of a first mode start switch). With the button being pressed by a user, a transfer to the initial setting mode for an injection amount is carried out. In this case, for example, after determining that the detection of a syringe mounting is made by the syringe detection switch 19 (S601 in FIG. 6), the controller 17 controls the display portion 3 so as to display information that prompts the user to press the initial setting button 6 for an injection amount. When the initial setting button 6 for an injection amount is pressed by the user, a transfer to the initial setting mode for an injection amount (S603 in FIG. 6) is carried out.

(2)

In the above embodiment, the initial setting for an injection amount is performed every time a drug is injected into a body, but this is not the only option.

Figure 11:
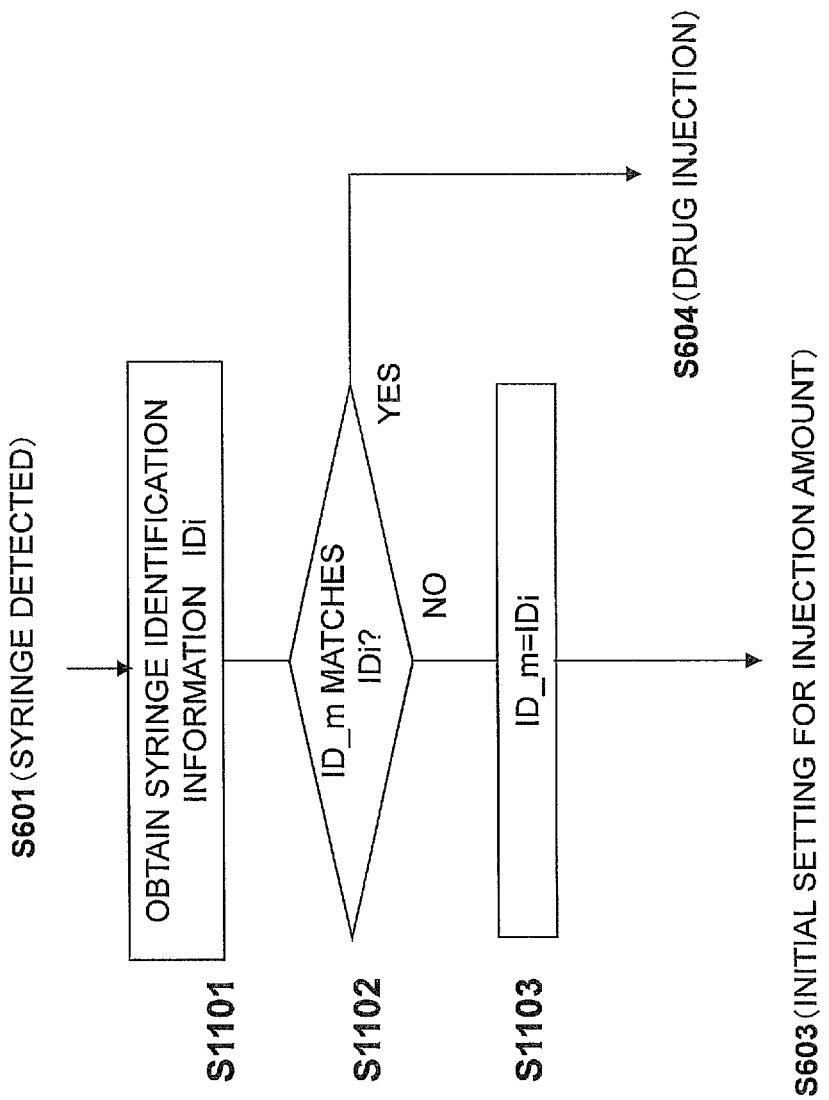
FIG. 11 is a flow chart of an operation of the pharmaceutical injection device according to another modified example.

If the material of the gasket 11 has a sufficiently small temperature characteristic, the initial setting mode for an injection amount may be implemented only when the syringe 9 is installed for the first time, not each time of drug injection. Then, the characteristic thus obtained may be used for the subsequent drug injections. In this case, for example, the controller 17 may perform a determination process as shown in FIG. 11 after detecting that the syringe is mounted (S601) as shown in FIG. 6. The controller 17 obtains identification information IDi provided to the mounted syringe 9 by means of a reading means (S1101). Then, the controller 17 compares the obtained identification information IDi with a value of identification information ID_m of the syringe 9, which was obtained at the time of mounting of a previous syringe and has been stored in the memory (S1102). As a result of the comparison, if the two match, a transfer to the drug injection mode (starting from S604 in FIG. 6) is carried out without implementing the initial setting mode for an injection amount. If the two do not match, the syringe 9 is a new one. Therefore, its identification information is stored as a value of ID_m (S1103), and a transfer to the initial setting mode for an injection amount is carried out (S603 in FIG. 6).

(3)

Figure 12:
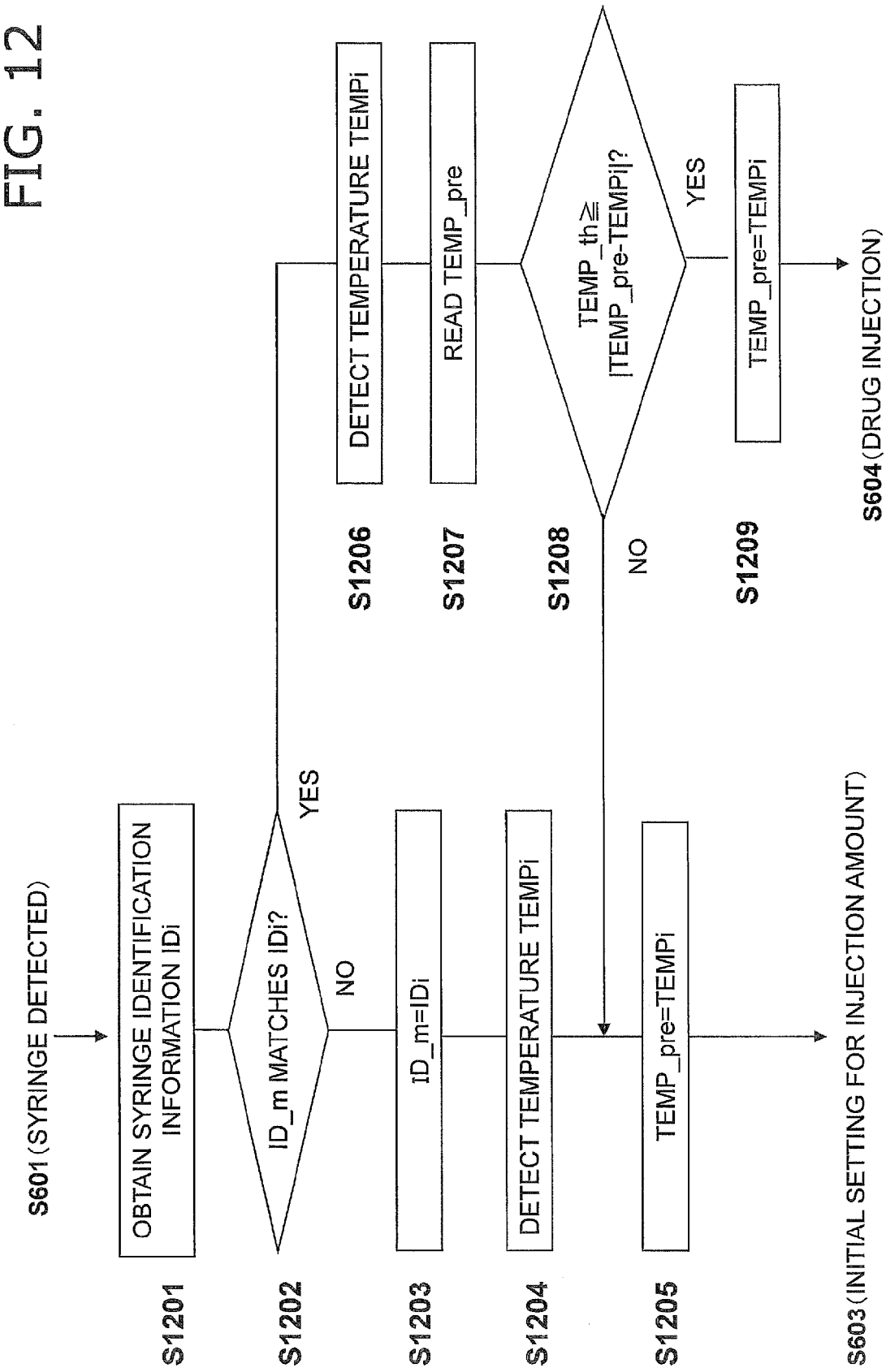
FIG. 12 is a flow chart of an operation of the pharmaceutical injection device according to still another modified example.

If the syringe 9 is mounted for the first time and the initial setting mode for an injection amount is implemented, the controller may further determine whether to implement a subsequent initial setting mode for an injection amount, in accordance with the ambient temperature of the syringe 9. In this case, for example, the process as shown in FIG. 12 is performed. The controller 17 obtains a value of the identification information IDi provided to the mounted syringe 9 by a reading means (S1201). Then, the controller 17 compares the obtained identification information IDi with the value of the identification information ID_m of the syringe stored in the memory (S1202). As a result of the comparison, if the two do not match, which means the syringe 9 is mounted for the first time, then the identification information IDi is recorded as a value of ID_m (S1203). Then, the temperature detection portion 175 of the controller 17 detects the ambient temperature TEMPi of the syringe 9 based on the output of the temperature sensor 24 (S1204), and the detected ambient temperature is recorded as a value of TEMP_pre in the memory (S1205). The controller 17 then implements the initial setting mode for an injection amount (starting from S603 in FIG. 6). As a result of the comparison in S1202, if the two match, by which it is determined that it is not the first time for the syringe 9 to be mounted, the process goes to the next operation. The temperature detection portion 175 of the controller 17 detects the ambient temperature TEMPi of the currently mounted syringe 9 based on the output of the temperature sensor 24 (S1206), and reads the value of TEMP_pre stored in the memory, that is, the ambient temperature of the syringe 9 at the time of the previous initial setting for an injection amount (S1207). Then, the controller 17 determines whether the difference between the detected value of TEMPi and the read value of TEMP_pre is within a predetermined threshold value TEMP_th (S1208). If it is greater than the predetermined threshold value TEMP_th, the deformation characteristic of the gasket 11 is likely to have changed due to the temperature change. Therefore, the value of TEMPi is stored as a value of TEMP_pre (S1205), and then the initial setting mode for an injection amount is implemented (starting from S603 in FIG. 6). On the other hand, if it is determined that the difference between the value of TEMPi and the value of TEMP_pre is within a predetermined threshold value TEMP_th in S1208, the value of TEMPi is stored as a value of TEMP_pre (S1209), and then, the drug injection mode (starting from S604 in FIG. 6) is implemented, using the set injection amount data according to the deformation characteristic of the gasket 11 that was previously obtained.

(4)

Furthermore, temperature dependency data of the deformation characteristic of the gasket 11, which was previously obtained, may be used. In this case, for example, the temperature dependency data of the deformation characteristic of the gasket 11 is experimentally obtained and stored in advance. As is the case with the above described example shown in FIG. 12, when the syringe 9 is mounted for the first time, the controller 17 implements the initial setting mode for an injection amount and obtains an ambient temperature of the syringe 9 at the time of initial setting for an injection amount based on the output of the temperature sensor 24. The controller 17 then obtains an ambient temperature of the syringe 9 again when a subsequent drug injection is performed and determines the difference between this obtained ambient temperature and the ambient temperature of the syringe 9 obtained at the time of the previous initial setting for an injection amount. Based on the temperature difference and the stored data of the temperature dependency data, the controller 17 may correct the injection amount setting data of the deformation characteristic of the gasket 11 which was previously obtained, and use the corrected injection amount setting data to implement the drug injection mode.

2 Second Embodiment

Figure 13:
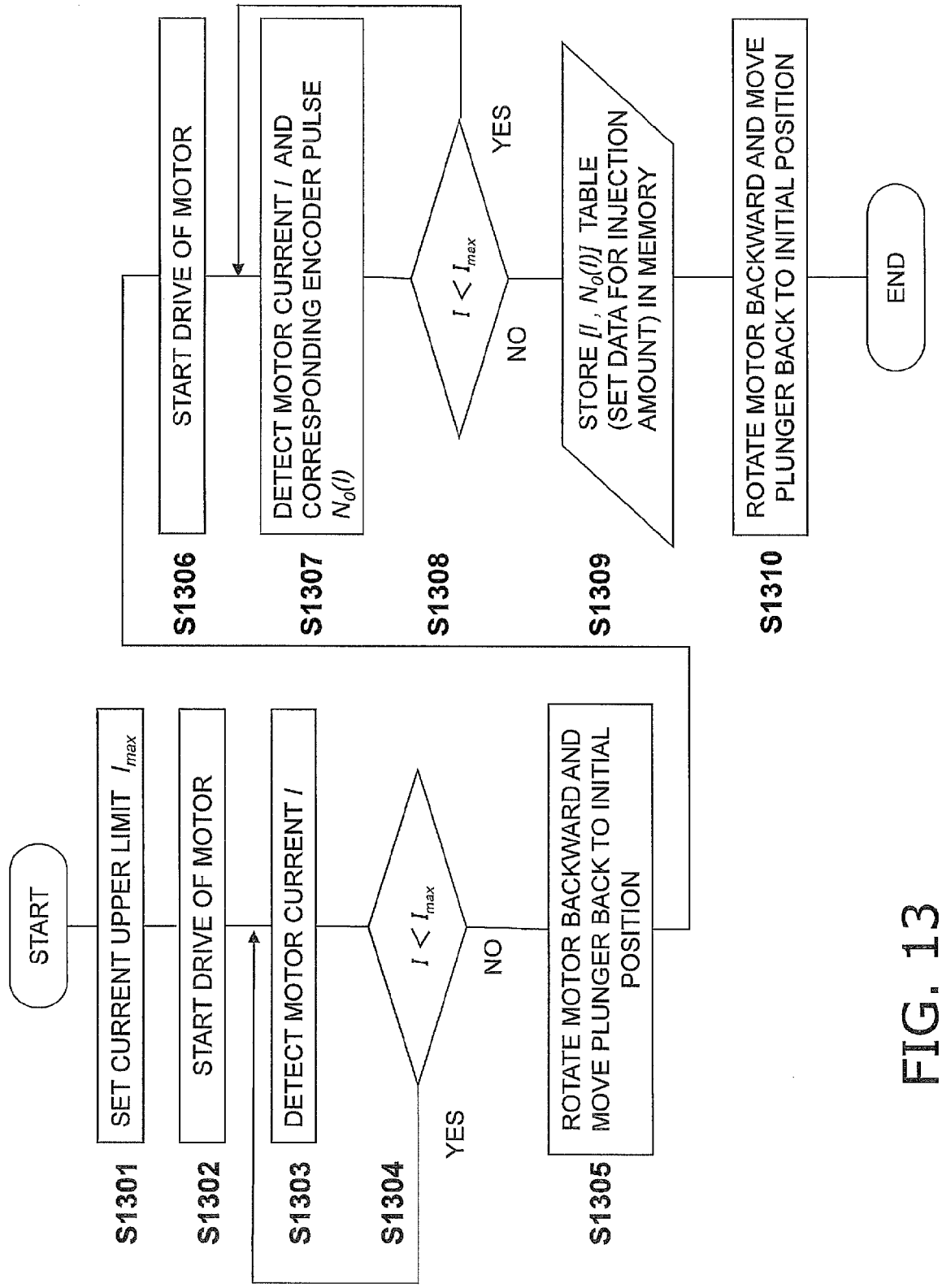
FIG. 13 is a flow chart of an operation of a pharmaceutical injection device according to the second embodiment.

FIG. 13 shows an operation of the pharmaceutical injection device 100 according to the second embodiment of the present invention. Since the configuration of the pharmaceutical injection device is the same as that of the above described one according to the first embodiment, the detailed description thereof will be omitted.

2-1 Operation

According this embodiment, the initial setting mode for an injection amount is implemented twice. Particularly, there is a case where the gasket 11 is stuck to an inner wall surface of the syringe 9 because the syringe 9 has been stored for a long period of time, for example. In this case, the plunger 13 is not likely to perform compression smoothly in the initial setting mode for an injection amount. Detailed description thereof will follow.

As is the case with the first embodiment, when the syringe 9 is mounted properly and the controller 17 determines that detection of a syringe mounting is made by the syringe detection switch 19, the controller 17 does a processing for obtaining setting data for an injection amount (from S601 to S603 in FIG. 6).

The controller 17 reads the current upper limit value $I_{max}$ that has been stored in the memory 18 (S1301).

Next, the controller 17 drives the motor 14 and presses the gasket 11 toward the injection needle mounting portion 10 by the feed screw 13a and the plunger 13 (S1302).

The rotation frequency of the motor 14 at this time is detected by the encoder 15, and at the same time, the motor current I is detected by the current detection sensor 16 (S1303). When the motor current I detected by the current detection sensor 16 goes beyond the value of $I_{max}$ (S1304), the controller 17 rotates the motor 14 backward to move the plunger 13 back to its initial position. As a result, the compressed gasket 11 is restored to its original shape as shown in FIG. 4 (S1305).

Then, the controller 17 starts driving the motor 14 again, and presses the gasket 11 toward the injection needle mounting portion 10 by the feed screw 13a and the plunger 13 (S1306).

The rotation frequency of the motor 14 at this time is detected by the encoder 15, and at the same time, the motor current I is detected by the current detection sensor 16 (S1307).

When the current detection sensor 16 has detected that the motor current I is equal to or greater than the value of $I_{max}$ (S1308), the controller 17 stops driving the motor 14. The data of the characteristic thus obtained (for example, characteristic A show in FIG. 9) is stored as [I, $N_0$ (I)] table in the memory 18 (S1309).

After that, the controller 17 rotates the motor 14 backward to move the plunger 13 back to its initial position (S1310).

Finally, the drug injection mode is started.

2-2 Effects

As described above, according to this embodiment, the plunger 13 is moved twice in the initial setting mode for an injection amount and then the characteristic data are obtained. This will prevent the gasket 11 from being stuck to the inner wall surface of the syringe 9, and therefore, it will increase the accuracy of the characteristic data. As a result, a drug injection can be done properly.

2-3 Modified Example

In this embodiment, the initial setting mode for an injection amount is implemented twice, but this is not the only option. It may be implemented three times or more, depending on how long the syringe 9 has been stored, for example.

Also, in this embodiment, the initial setting mode for an injection amount may be implemented only when the syringe 9 is mounted for the first time.

3 Third Embodiment

The third embodiment will be described by reference to FIG. 14 through FIG. 17. Since the configuration of the pharmaceutical injection device 100 is the same as that of the above described one according to the first embodiment, the detailed description thereof will be omitted.

3-1 Operation

In the drug injection mode implemented by the drug injection apparatus 100, after the drug injection is completed, the motor 14 is rotated backward to move the plunger 13 back to its initial position. In this case, an error can occur between a target drug injection amount and an actual drug injection amount (hereinafter, called an injection amount error).

Figure 14:
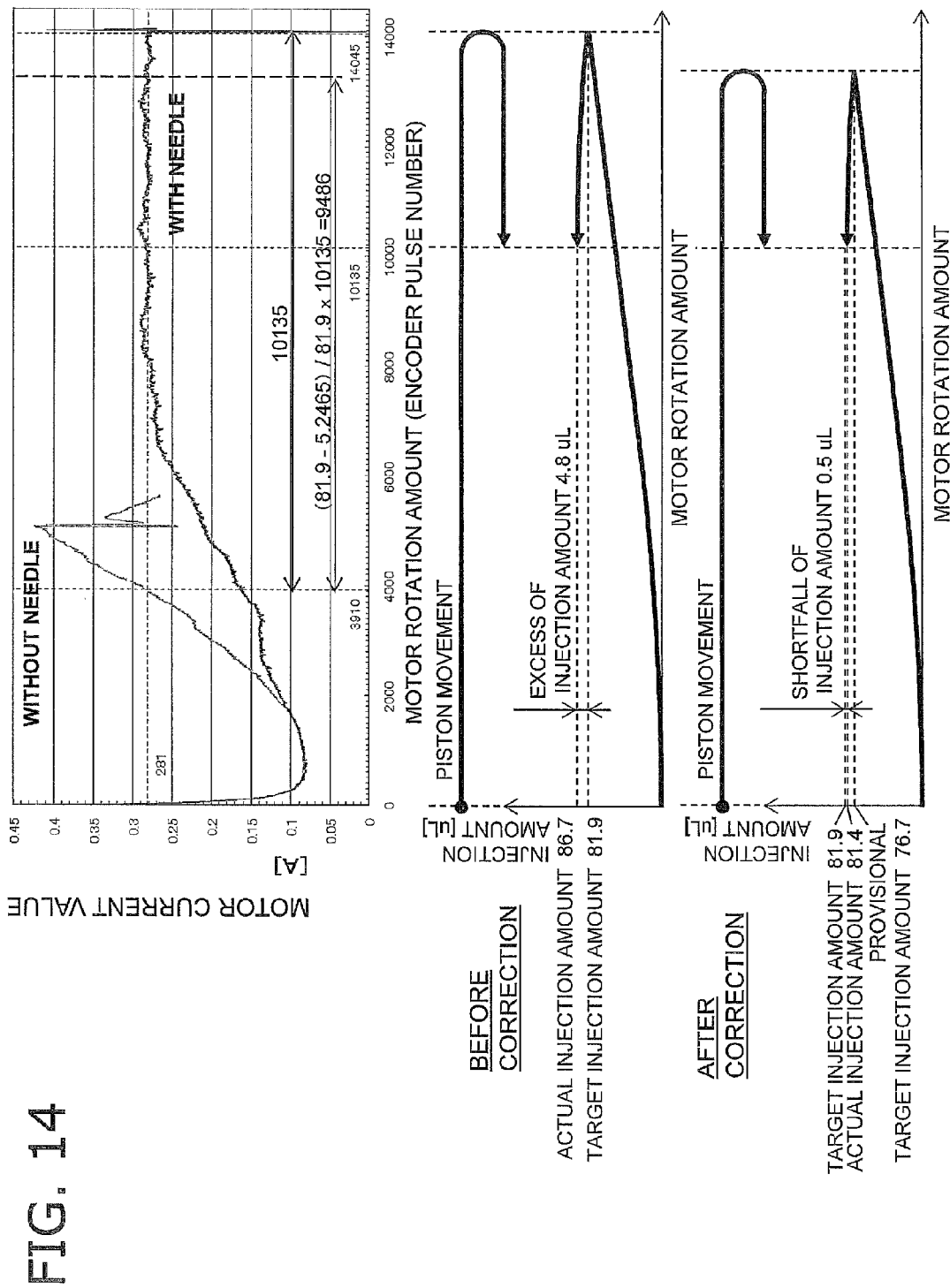
FIG. 14 is a diagram for explaining a relation between a backward rotation of a motor and an injection amount of drug.

As shown in FIG. 14, for example, when the set drug injection amount is, for example, 81.9 μL, the motor rotation amount or the encoder pulse number that corresponds to the amount of 81.9 μL is calculated to be 10135 pulses (based on Formula 1, for example). The encoder pulse number $N_0$ (I(N)) that corresponds to a deformation amount of the gasket 11 is calculated to be 3910 pulses. When the drug injection is performed under the condition of $N_R$=10135, when the value of (N)−$N_0$ (I(N)) reaches the value of $N_R$ (=10135), that is, when N=14045 is satisfied, the motor 14 is rotated backward by the degree that corresponds to 3910 pulses of $N_0$ (I(N)). As a result, the motor 14 stops rotating at a position that corresponds to 10135 pulses of $N_R$ from its initial position. It is presumed that, when the value of (N)−$N_0$ (I(N)) reaches the value of $N_R$ (=10135), the target drug injection amount 81.9 μL has been administered. However, while the motor 14 is rotated backward by the degree that corresponds to 3910 pulses and until it stops the backward rotation, the drug is likely to come out of the syringe that is being exposed to high pressure due to the deformation of the gasket. This will cause an excess injection amount of drug to come out of the syringe during the backward rotation of the motor 14. An actual experiment showed that there was an excess injection amount of 4.8 μL when the drug injection is performed under the above described condition.

Figure 15:
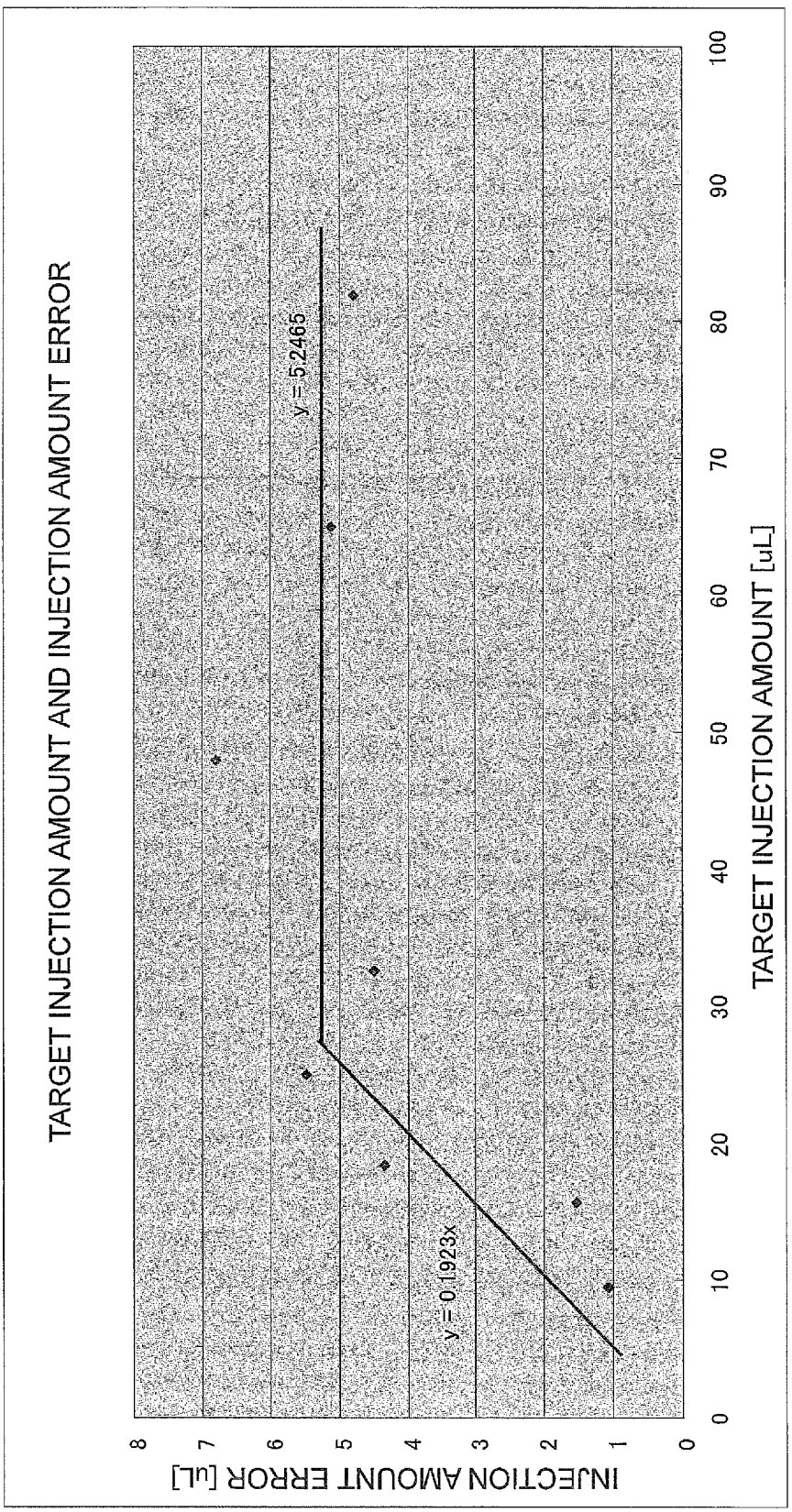
FIG. 15 is a graph showing a relation between a target injection amount of drug and an error in an injection amount of drug.

FIG. 15 shows a graph indicating a relation between a target injection amount of a drug and an injection amount error which is an excess or a shortfall in the injection amount). As shown in FIG. 15, when the target injection amount is small, the target injection amount is proportional to the injection amount error. As the target injection amount is greater, the injection amount error will be a constant value. This is because, as the injection amount gets to a certain amount, the gasket does not deform further, which makes its deformation amount constant.

According to the correlation between the target injection amount and the injection amount error (hereinafter, called correction error data), when the target injection amount is 81.9 μL, the injection amount error is +5.2465 μL. Accordingly, as shown in FIG. 14, a provisional target injection amount is set to 76.6535 μL, which is calculated by subtracting the value of +5.2465 μL of the injection amount error from the value of 81.9 μL of the target injection amount. The motor rotation amount which corresponds to the provisional target injection amount and is 9486 pulses in this example is set as a value of $N_R$. Then, the drug injection is performed. Accordingly, at the time when the value of N−$N_0$ (I(N)) has reached the value of $N_R$ (=9486), the drug has been administered by the provisional target injection amount of 76.6535 μL. After that, the motor 14 is rotated backward to a position that corresponds to 10135 pulses from the initial position, by which an injection amount of 5.2465 μL is injected. As a result, the total injection amount amounts to the target injection amount of 81.9 μL (or its approximation as shown in the drawing).

Figure 16:
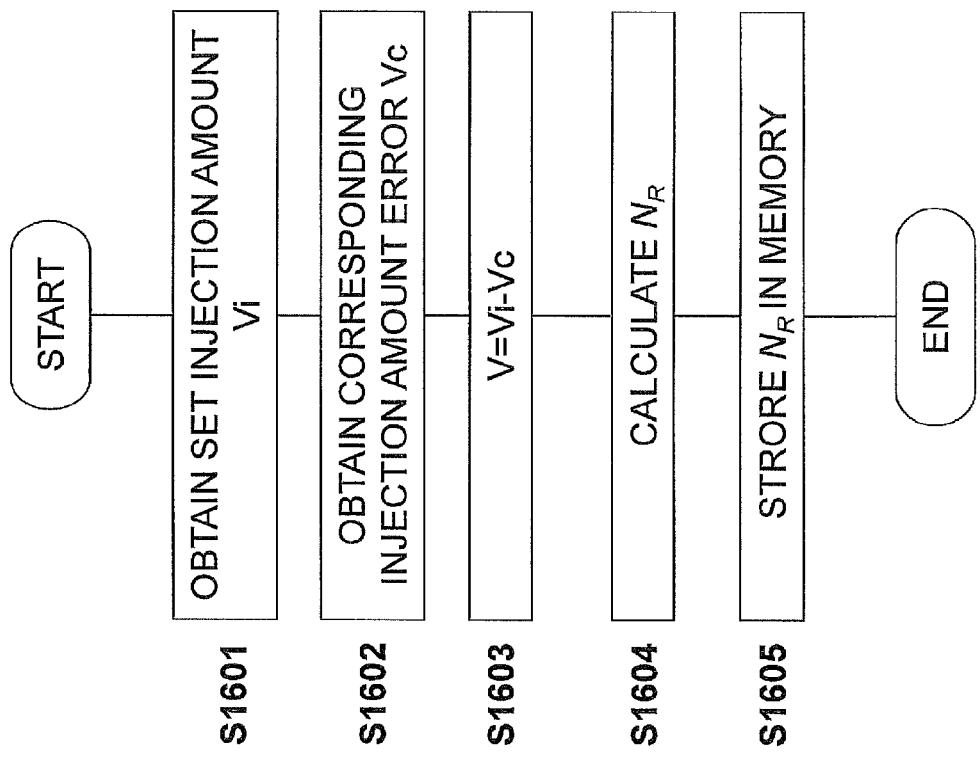
FIG. 16 is a flow chart of an operation of the pharmaceutical injection device according to the third embodiment.

FIG. 16 shows a process carried out by the pharmaceutical injection device 100 according to this embodiment for calculating the value $N_R$ of the encoder pulse number that corresponds to a set injection amount.

First, the controller 17 obtains a value of the set injection amount Vi of the drug (S1601).

Next, the controller 17 reads the correction error data (FIG. 15) that have been stored in the memory 18, and obtains a value of the injection amount error Vc that corresponds to the set injection amount Vi (S1602).

Then, the controller 17 corrects the set injection amount of the drug where the set injection amount V=Vi−Vc (S1603).

Using the set injection amount V, the controller calculates an encoder pulse number $N_R$ that corresponds to the set injection amount (S1604). The above described Formula 1 is used to calculate the encoder pulse number $N_R$.

The controller 17 then stores the calculated encoder pulse number $N_R$ in the memory 18 (S1605). The pharmaceutical injection device 100 performs a drug injection (FIG. 8) using the calculated encoder pulse number $N_R$.

3-2 Effects

In the above embodiment, the set injection amount of a drug is corrected using correction error data that have been stored in the memory. Therefore, it is possible to prevent an error in the drug injection amount, which is likely to occur while the motor 14 is rotated backward after the completion of the drug injection. Accordingly, the drug injection can be done with a high degree of accuracy.

Figure 17:
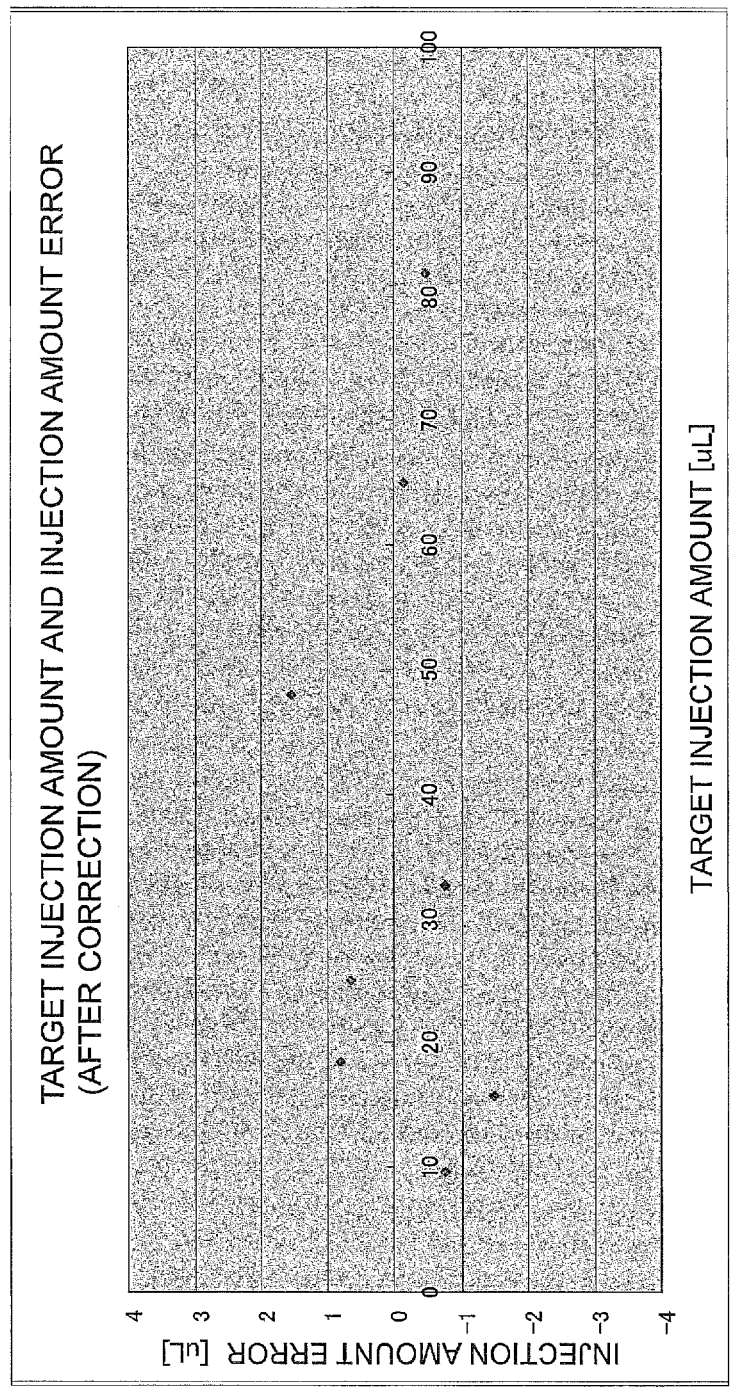
FIG. 17 is a graph showing an error in an injection amount of drug with respect to a target injection amount of drug after correction in the pharmaceutical injection device according to the third embodiment.

FIG. 17 shows an injection amount error with respect to the target injection amount, which is an excess or a shortfall in an injection amount, after correction of the set injection amount according to the above embodiment. As shown in FIG. 17, the injection amount error of a drug has an approximation value of 0 no matter what the target injection amount is.

3-3 Modified Example

In the third embodiment as described above, the set injection amount of a drug is corrected according to the relation between the target drug injection amount and the correction error in the injection amount, but this is not the only option.

Figure 18:
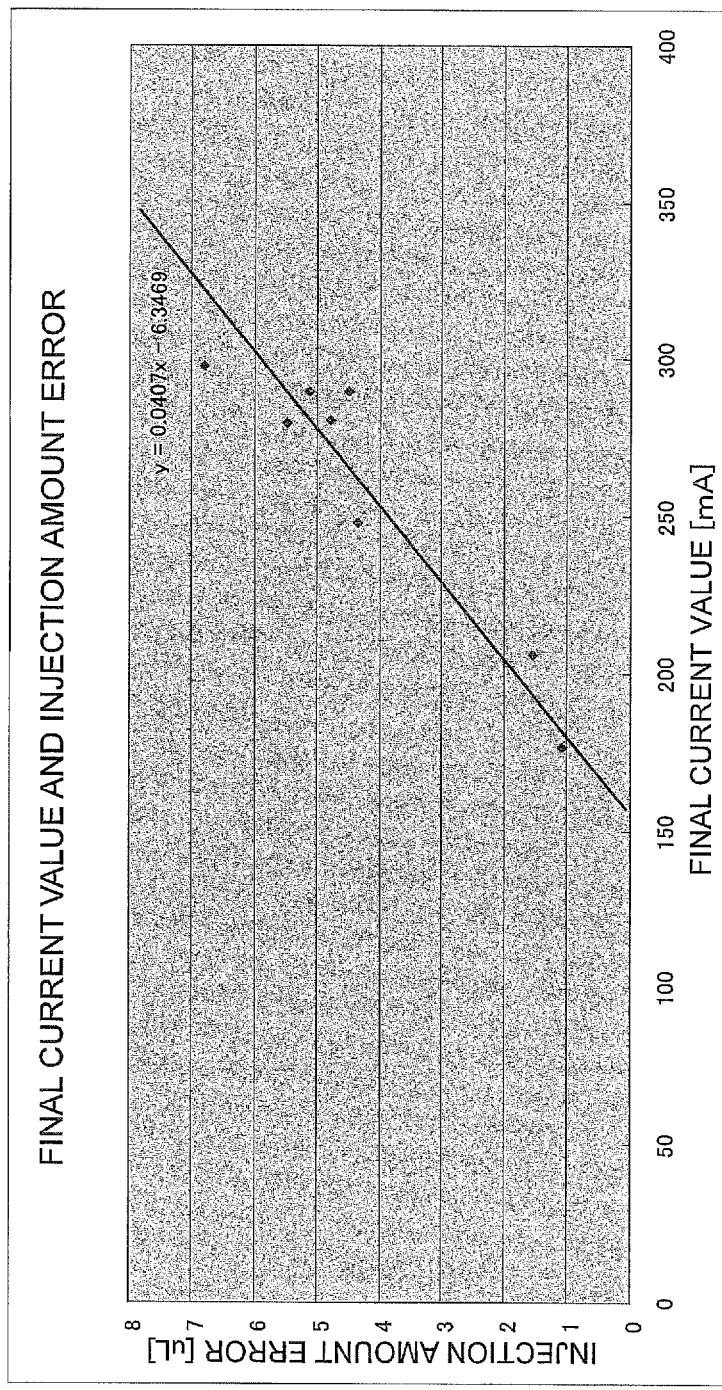
FIG. 18 is a graph showing a relation between a final current value and an error in the injection amount of drug.

FIG. 18 shows a relation between a final current value (a current value right before the backward rotation of the motor 14) and an injection amount error (hereinafter, called correction error data). As shown in FIG. 18, the final current value has a certain proportional relation to the injection amount error. Based on this relation, the set injection amount of a drug is corrected. In this case, the correction error data as shown in FIG. 18 are stored in the memory 18 in advance. Then, the set injection amount of the drug is corrected as is the case with the process shown in FIG. 16. The encoder pulse number $N_R$ that corresponds to the corrected set injection amount is calculated according to, for example the above described Formula 1.

Figure 19:
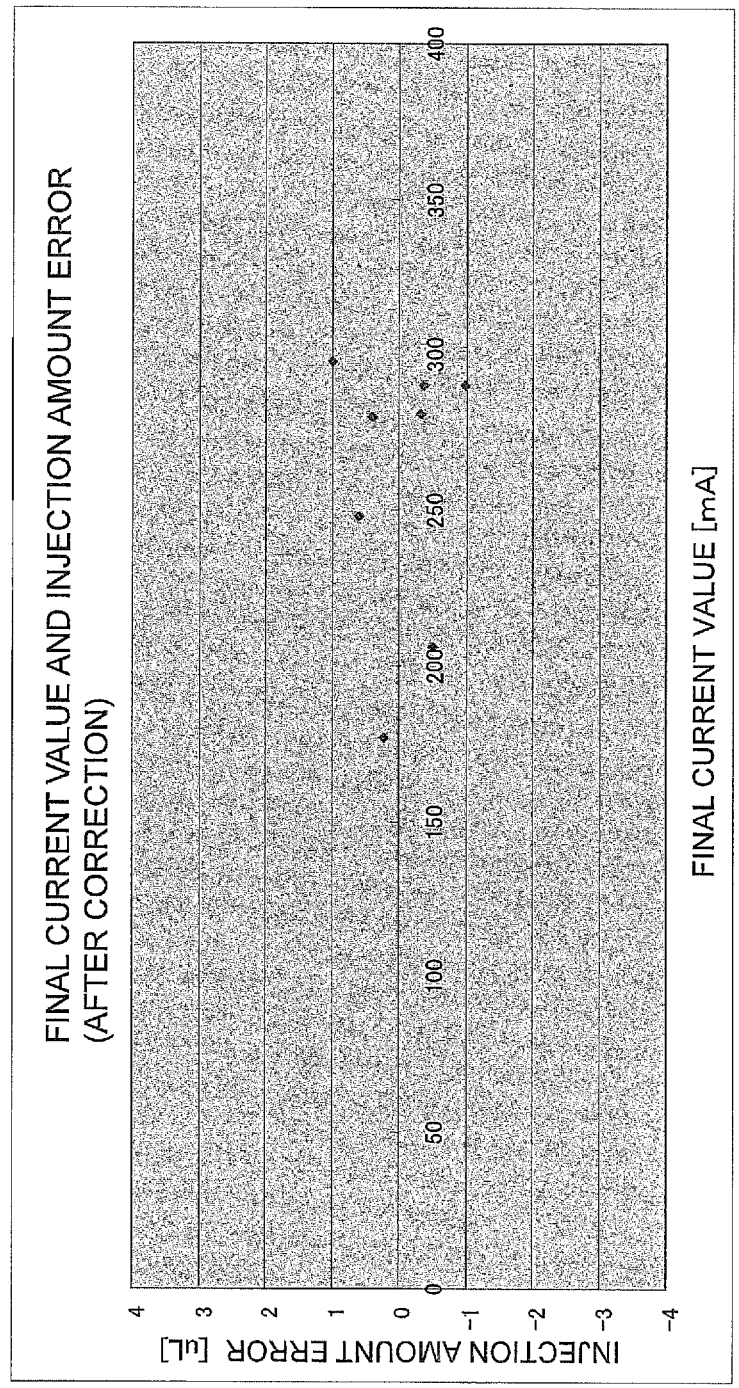
FIG. 19 is a graph showing an error in an injection amount of drug with respect to a final current value after correction in the pharmaceutical injection device according to a modified example of the third embodiment.

FIG. 19 shows an error in the injection amount (an excess or a shortfall in the injection amount) with respect to the final current value, as a result of correction of the set injection amount according to the above modified example. As shown in FIG. 19, the error in the drug injection amount has an approximation value of 0 no matter what the final current value is.

4 Other Embodiments

The pharmaceutical injection device 100 according to the above embodiments includes the gasket 11 provided in the syringe 9, which is made from a rubber material and is pressed by the plunger 13, but this is not the only option. The gasket 11 may be any elastic member that is made from a material with which a drug can be sealed in the syringe and which is deformable by press.

Furthermore, the order for carrying out processes in the above embodiments is not limited to what is described above, but may be changed as far as it is within the scope of the present invention.

INDUSTRIAL APPLICABILITY

The pharmaceutical injection device according to this disclosure is applicable to, for example, a pharmaceutical injection device for injecting a drug into a human body for treating illness of any kind.

The invention claimed is:

1. A pharmaceutical injection device comprising:
   a syringe including a first end side, a second end side, an injection needle mounting portion, an elastic member, and a drug;
   the injection needle mounting portion disposed at the first end side of the syringe;
   the elastic member disposed at the second end side of the syringe;
   a syringe mounting portion configured to mount the syringe;
   a plunger operable to press the elastic member toward the injection needle mounting portion and deform the elastic member;
   a motor operable to drive the plunger;
   an encoder operable to detect a rotation amount of the motor;
   a controller connected to the encoder and operable to:
      control a driving of the motor,
      obtain a first motor rotation amount, and
      control a rotation of the motor at a time of drug injection;
   the first motor rotation amount corresponding to a deformation amount of the elastic member; and
   the rotation of the motor at a time of drug injection being in accordance with the first motor rotation amount.

2. The pharmaceutical injection device according to claim 1, further comprising:
   a preset motor rotation amount corresponding to a set injection amount; and
   the controller is further operable to control the rotation of the motor at the time of drug injection such that the motor rotates by an amount that is equal to a sum of the first motor rotation amount and the preset motor rotation amount.

3. The pharmaceutical injection device according to claim 2, wherein:
   the controller is further operable to rotate the motor backward when the encoder detects that the motor has rotated the amount that is equal to the sum of the first motor rotation amount and the preset motor rotation amount.

4. The pharmaceutical injection device according to claim 1, further comprising:
   a current detection sensor connected to the controller, and operable to detect a current driving the motor;
   a predetermined value of the current driving the motor that drives the motor the first rotation amount; and
   the controller is further operable to obtain the predetermined value of the current driving the motor.

5. The pharmaceutical injection device according to claim 1, further comprising:
   an injection needle; and
   the controller is further operable to:
      implement a first operation mode obtaining the first motor rotation amount from the encoder in a state in which the injection needle is not mounted,
      after implementing the first operation mode, implement a second operation mode injecting the drug while obtaining a second motor rotation amount from the encoder in a state in which the injection needle is mounted on the injection needle mounting portion, and
      in the second operation mode, stop the injection of the drug when a difference between the first motor rotation amount and the second motor rotation amount is equal to or greater than a third motor rotation amount, the third motor rotation amount corresponding to the set injection amount.

6. The pharmaceutical injection device according to claim 5, further comprising:
   a current detection sensor connected to the controller and operable to detect a current driving the motor; and
   wherein in the second operation mode, the controller stops the injection of the drug when the difference between the first motor rotation amount and the second motor rotation amount is equal to or greater than the third motor rotation amount,
   the first motor rotation amount being obtained at a predetermined value of the current detected by the current detection sensor.

7. The pharmaceutical injection device according to claim 5, further comprising;
   a first mode start switch connected to the controller and operable to start the first operation mode.

8. The pharmaceutical injection device according to claim 5, further comprising:
   a second mode start switch connected to the controller and operable to start the second operation mode.

9. The pharmaceutical injection device according to claim 5, wherein:
   the controller is further operable to implement the second operation mode after having implemented the first operation mode two or more times.

10. The pharmaceutical injection device according to claim 5, wherein:
    the controller implements the first operation mode only one time after each time the syringe is mounted.

11. The pharmaceutical injection device to claim 3, wherein:
    the controller corrects the set injection amount based on an error in an injection amount of the drug, the error being caused by the backward rotation of the motor.

12. The pharmaceutical injection device according to claim 11, wherein:
    the error in the injection amount of the drug is obtained based on a relationship between the error and the set injection amount.

13. The pharmaceutical injection device according to claim 11, wherein:
    the error in the injection amount of the drug is obtained based on a relationship between the error and a value of a current driving the motor before the backward rotation of the motor.

14. The pharmaceutical injection device according to claim 5, wherein:
    the controller is further operable to detect an ambient temperature of the syringe mounted on the syringe mounting portion, and implements the first operation mode in accordance with the detected ambient temperature of the syringe.

15. A pharmaceutical injection device, comprising:
    a syringe including a first end side, a second end side, an injection needle mounting portion, an elastic member, and a drug;
    the injection needle mounting portion disposed at the first end side of the syringe;
    the elastic member disposed at the second end side of the syringe;

a syringe mounting portion configured to mount the syringe;

a plunger operable to press the elastic member toward the injection needle mounting portion and deform the elastic member;

a motor operable to drive the plunger;

an encoder operable to detect a rotation amount of the motor;

a memory connected to the controller;

an injection needle; and a controller connected to the current detection sensor and the encoder, the controller operable to:

control a driving of the motor;

implement a first operation mode obtaining a first motor rotation amount from the encoder in a state in which the injection needle is not mounted on the injection needle mounting portion;

after implementing the first operation mode, implement a second operation mode injecting the drug while obtaining a second motor rotation amount from the encoder in a state in which the injection needle is mounted on the injection needle mounting portion;

obtain the second motor rotation amount, the second motor rotation amount being a rotation frequency of the motor at a time when a value of the current driving the motor reaches a predetermined value in the second operation mode;

obtain the first motor rotation amount from the memory, the first motor rotation amount corresponding to a predetermined value of the current; and stop the injection of the drug when a difference between the obtained first motor rotation amount and the obtained second motor rotation amount is equal to or greater than a third motor rotation amount that corresponds to the set injection amount.

* * * * *